Oct. 12, 1971 C. B. McCANNON Plant Pat. 3,072
ROSE PLANT
Filed July 3, 1968
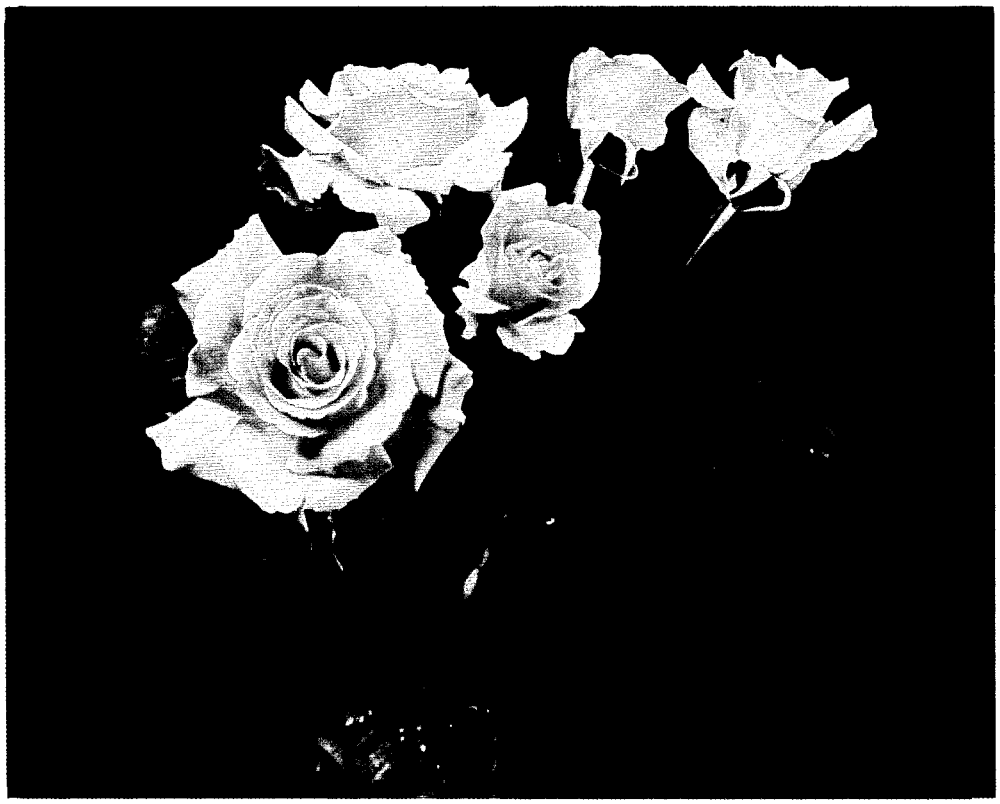
INVENTOR.
CHARLES B. McCANNON
BY Rummler & Snow
ATTYS.

United States Patent Office

Plant Pat. 3,072
Patented Oct. 12, 1971

3,072
ROSE PLANT

Charles B. McCannon, Mount Clemens, Mich., assignor to Frank J. Munt Flowers, Inc., Mount Clemens, Mich.

Filed July 3, 1968, Ser. No. 742,469
Int. Cl. A01h 5/00
U.S. Cl. Plt.—18 1 Claim

ABSTRACT OF THE DISCLOSURE

A new variety of rose plant having very large deep pink blooms borne singly on sturdy thick stems and particularly characterized by a new and different color, a pleasant tea fragrance, numerous large petals, and excellent lasting quality both on the plant and as cut flowers; the new plant being a greenhouse rose of vigorous upright growth which blooms profusely in any season.

BACKGROUND OF THE INVENTION

My new variety of rose plant originated as a sport of Pink Sensation (Plant Patent #1,584) discovered by me among greenhouse growth at Mount Clemens, Mich. in the fall of 1965. The different and pleasing color of the sport prompted its individual propagation to determine its commercial possibilities and subsequent asexual propagation under my direction, at Mount Clemens, Mich., by budding, demonstrated that the new variety thus established had further advantageous characteristics of growth, bloom production, flower size and fragrance and excellent lasting quality which indicated very good prospects for commercial exploitation.

Successive generations of asexually propagated plants of the new variety have shown that its new, distinctive and advantageous characteristics are fixed and hold true in all respects. Present propagation is done by budding at Livermore Calif., where the new variety has been thoroughly tested and observed under commercial production.

DESCRIPTION OF THE DRAWING

My new variety of rose plant is illustrated by the accompanying full color drawing which shows typical specimens of buds, partially opened and fully opened blooms, and the general nature of the plant foliage.

DESCRIPTION OF THE NEW PLANT VARIETY

The following is a detailed description of my new variety of rose plant with color designation according to the Horticultural Color Chart of the British Colour Council.

*The Plant*

Origin: Sport
Parent Variety: Pink Sensation, Plant Patent #1,584.
Classification:
*Botanic.*—*Rosa hybrida.*
*Commercial.*—Greenhouse rose, "Shocking Pink."
Form: Bush, upright and branching.
Height: At least 8 to 10 feet, depending on cultural treatment.
Growth: Vigorous and erect with sturdy, very strong canes.
Foliage: Quantity—abundant, 4 to 5 leaves per foot of stem.
*Size of leaf.*—About 6¾ inches long
*Shape of leaf.*—Odd-pinnately compound

*Leaflets.*—5 in number, ovate in shape with acute apex, rounded base and serrated margins.
*Texture.*—Leathery and smooth
*Color.*—Upper side—parsley green 00962. Under side—spinach green 0960/3.
*Ribs and veins.*—Alternately pinnate and netted.
*Petioles.*—Length—3⅛ to 3⅞ inches
*Thorns.*—None; spines: None.
*Prickles.*—Occasional. Size: 3/16 to 5/16 inch long. Color: Dresden Yellow 64/2, with anthocyanin tinge

*Bud*

Form: Ovoid.
Size: 1 1/16 inch in diameter.
Opening rate: Slow.
Color: When sepals first divide—Rose Bengal 25. When sepals begin to unfurl—Rose Bengal 25/1.
Sepals: Hooded over bud; spear shaped with 2 or 3 branched and the remainder not branched; curl back upon dividing.
Calyx: Sepals forming calyx are always separated and are of average size. Calyx is split from the beginning, smooth on the outside and hairy on the inside.
Peduncle: Erect, 3¾ to 4¼ inches long and smooth. Color: Scheeles Green 860/1.

*The flower*

Blooming habit: Recurrent. Blooms profusely in any season (in greenhouse)
Size: Large. 5 inches in diameter, 3 inches deep.
Borne: Singly.
Shape: Cup shaped when bloom first opens; form changes later with an increase in diameter, in proportion to the depth.
Petalage: 25 petals in imbricate arrangement.
*Form.*—Roundish
*Color.*—Outer petal—Rose Bengal 25/2 with Uranium Green 63/3 at the base. Inside petal—Rose Bengal 25/1. Reverse side—Rose Bengal 25/2.
*Petaloids.*—5 in number; ⅜ inch to 1½ inches in size. Color: Rose Bengal 25/1.
*Texture.*—Leathery. Appearance: Velvety.
*Discoloration after full bloom.*—None.
Peduncle: Sturdy and upright; 4 5/16 to 5⅛ inches long; Color—Scheeles Green 860/1.
Fragrance: Distinctive and pleasant tea fragrance.
Lasting quality: Excellent, on plant and as a cut flower. Petals stay on stem for two weeks.
Persistence: Strong—hangs on stem and dries.
Disease resistance: Moderately resistant to mildew as observed at Mount Clemens, Mich. and Livermore Calif.

*Reproductive organs*

Stamens:
*Anthers.*—150 in cyclic arrangement, each about 3/16 inch long.
*Filaments.*—½ inch long, Fuchsine Pink 627/1 in color.
Pollen: Color—Buttercup Yellow 5/2.
Pistils: Number—140; length 3/16 inch maximum.
Stigmas: Color—Primrose Yellow 601/3.
Ovaries: Hypanthial.

*Fruit*

The fruit is fertile, round in shape and of Orient Red 819 in color at maturity.

My new variety of rose plant most nearly resembles its parent Pink Sensation (P.P. 1,584). It differs in color. however, being of a much deeper and very distinctive pink. The blooms have larger petals of good substance, are of very excellent keeping qualities, and have a distinctive fragrance. The plant grows vigorously with good strong canes and thick stem for the blooms. Prickles are rare and the foliage is abundant with fairly large leaves growing close to each other along the length of the stem.

I claim:

1. A new and distinct variety of rose plant substantially as herein shown and described, characterized by the Rose Bengal color of its blooms, its capability to bloom profusely in any season, its vigorous growth habit, and the fragrance and long lasting quality of its blooms No references cited.

ROBERT E. BAGWILL, Primary Examiner